US00PP28533P3

(12) United States Plant Patent
Wain

(10) Patent No.: US PP28,533 P3
(45) Date of Patent: Oct. 17, 2017

(54) ***CHRYSANTHEMUM* PLANT NAMED 'FIDAYSOFLA'**

(50) Latin Name: *Chrysanthemum×morifolium*
Varietal Denomination: Fidaysofla

(71) Applicant: Peter Wain, Locks Heath (GB)

(72) Inventor: Peter Wain, Locks Heath (GB)

(73) Assignee: Dümmen Group B.V., De Lier (NL)

( * ) Notice: Subject to any disclaimer, the term of this patent is extended or adjusted under 35 U.S.C. 154(b) by 108 days.

(21) Appl. No.: 14/757,067

(22) Filed: Nov. 11, 2015

(65) Prior Publication Data

US 2017/0135269 P1 May 11, 2017

(51) Int. Cl.
*A01H 5/02* (2006.01)

(52) U.S. Cl.
USPC ..... Plt./287

(58) Field of Classification Search
USPC ..... Plt./287
See application file for complete search history.

*Primary Examiner* — Anne Grunberg
(74) *Attorney, Agent, or Firm* — C. A. Whealy

(57) ABSTRACT

A new and distinct cultivar of *Chrysanthemum* plant named 'Fidaysofla', characterized by its upright to outwardly spreading and uniformly mounded plant habit; moderately vigorous growth habit; freely branching habit; dense and full plant form; uniform and freely flowering habit; medium-size decorative-type inflorescences with yellow and orange red bi-colored ray florets; early season flowering habit; and good garden performance.

1 Drawing Sheet

Botanical designation: *Chrysanthemum×morifolium.*
Cultivar denomination: 'FIDAYSOFLA'.

BACKGROUND OF THE INVENTION

The present invention relates to a new and distinct *Chrysanthemum* plant, botanically known as *Chrysanthemum×morifolium*, commercially grown as a garden *Chrysanthemum* plant and hereinafter referred to by the name 'Fidaysofla'.

The new *Chrysanthemum* plant is a product of a planned breeding program conducted by the Inventor in Fareham, Hampshire, United Kingdom. The objective of the breeding program is to create new early season flowering garden *Chrysanthemum* plants with numerous attractive inflorescences.

The new *Chrysanthemum* plant originated from a cross-pollination made in January, 2011 by the Inventor in Fareham, Hampshire, United Kingdom of a proprietary selection of *Chrysanthemum×morifolium* identified as code number 83420, not patented, as the female, or seed, parent with a proprietary selection of *Chrysanthemum×morifolium* identified as code number 83261, not patented, as the male, or pollen, parent. The new *Chrysanthemum* plant was discovered and selected by the Inventor as a single flowering plant from within the progeny of the stated cross-pollination in a controlled greenhouse environment in Fareham, Hampshire, United Kingdom in September, 2011.

Asexual reproduction of the new *Chrysanthemum* plant by terminal vegetative cuttings was first conducted in Fareham, Hampshire, United Kingdom in December, 2011. Asexual reproduction by terminal vegetative cuttings has shown that the unique features of this new *Chrysanthemum* plant are stable and reproduced true to type in successive generations.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Fidaysofla'. These characteristics in combination distinguish 'Fidaysofla' as a new and distinct *Chrysanthemum* plant:

1. Upright to outwardly spreading and uniformly mounded plant habit.
2. Moderately vigorous growth habit.
3. Freely branching habit; dense and full plant form.
4. Uniform and freely flowering habit.
5. Medium-size decorative-type inflorescences with yellow and orange red bi-colored ray florets.
6. Early season flowering habit, grown under natural season conditions, plants flower in mid to late August in the United Kingdom.
7. Good garden performance.

Plants of the new *Chrysanthemum* can be compared to plants of the female parent selection. Plants of the new *Chrysanthemum* differ from plants of the female parent selection in the following characteristics:

1. Under natural season conditions, plants of the new *Chrysanthemum* flower earlier than plants of the female parent selection.
2. Plants of the new *Chrysanthemum* and the female parent selection differ in ray floret color as plants of the female parent selection have inflorescences with red-colored ray florets.

Plants of the new *Chrysanthemum* can be compared to plants of the male parent selection. Plants of the new *Chrysanthemum* differ from plants of the male parent selection in ray floret color as plants of the male parent selection have inflorescences with pink and white-colored ray florets.

Plants of the new *Chrysanthemum* can be compared to plants of *Chrysanthemum×morifolium* 'Conaco Bronze', not patented. In side-by-side comparisons conducted in Fareham, Hampshire, United Kingdom, plants of the new *Chrysanthemum* differed from plants of 'Conaco Bronze' in the following characteristics:

1. Grown under natural season conditions, plants of the new *Chrysanthemum* flowered about one month earlier than plants of 'Conaco Bronze'.
2. Plants of the new *Chrysanthemum* and 'Conaco Bronze' differed in ray floret color as plants of 'Conaco Bronze' had inflorescences with solid bronze-colored ray florets.

BRIEF DESCRIPTION OF THE PHOTOGRAPH

The accompanying photograph illustrates the overall appearance of the new *Chrysanthemum* plant showing the colors as true as it is reasonably possible to obtain in colored reproductions of this type. Colors in the photograph may differ slightly from the color values cited in the detailed botanical description which accurately describe the colors of the new *Chrysanthemum* plant. The photograph is a side perspective view of a typical flowering plant of 'Fidaysofla' grown in a 19-cm container.

DETAILED BOTANICAL DESCRIPTION

The aforementioned photograph and following observations and measurements describe plants grown during the winter in 19-cm containers in a glass-covered greenhouse in Fareham, Hampshire, United Kingdom and under cultural practices typical of commercial garden *Chrysanthemum* production. During the production of the plants, day and night temperatures ranged from 17° C. to 21° C. and light levels averaged 6,000 lux. Plants were grown under long day/short night conditions for eight weeks (including propagation period) and then grown under short day/long night conditions to induce inflorescence initiation and development. Plants were 14 weeks old when the photograph and detailed description were taken. In the following description, color references are made to The Royal Horticultural Society Colour Chart, Fifth Edition, except where general terms of ordinary dictionary significance are used.

Botanical classification: *Chrysanthemum×morifolium* 'Fidaysofla'.

Parentage:

*Female, or seed, parent.*—Proprietary selection of *Chrysanthemum ×morifolium* identified as code number 83420, not patented.

*Male, or pollen, parent.*—Proprietary selection of *Chrysanthemum ×morifolium* identified as code number 83261, not patented.

Propagation:

*Type.*—Terminal vegetative cuttings.

*Time to initiate roots, summer.*—About ten days at temperatures about 21° C.

*Time to initiate roots, winter.*—About twelve days at temperatures about 21° C.

*Time to produce a rooted young plant, summer.*—About three weeks at temperatures about 21° C.

*Time to produce a rooted young plant, winter.*—About four weeks at temperatures about 21° C.

*Root description.*—Fine, fibrous; typically light brown in color, actual color of the roots is dependent on substrate composition, water quality, fertilizer type and formulation, substrate temperature and physiological age of roots.

*Rooting habit.*—Freely branching; dense.

Plant description:

*Plant and growth habit.*—Herbaceous decorative-type garden *Chrysanthemum*; stems upright to outwardly spreading giving a uniformly mounded appearance to the plant; numerous lateral branches and relatively short internodes, dense and full plant form; moderately vigorous growth habit.

*Plant height.*—About 20 cm.

*Plant width.*—About 31 cm.

*Main stem diameter.*—About 5 mm.

*Branching habit.*—Freely branching habit; about twelve lateral branches develop after removal of terminal apex (pinching).

*Lateral branches.*—Length: About 14.5 cm. Diameter: About 3 mm. Internode length: About 1.5 cm. Strength: Strong. Aspect: About 45° from the main stem and then bending upwardly. Texture: Fine pubescence. Color: Close to 139D.

Leaf description:

*Arrangement.*—Alternate, simple.

*Length.*—About 4.5 cm.

*Width.*—About 4.2 cm.

*Shape.*—Palmately-lobed; roughly ovate with three to five lobes.

*Apex.*—Broadly acuminate.

*Base.*—Attenuate.

*Margin.*—Slightly dentate and palmately lobed; sinuses between lateral lobes divergent.

*Texture, upper and lower surfaces.*—Fine pubescence; slightly rough; veins prominent on lower surface.

*Color.*—Developing leaves, upper surface: Close to 136B. Developing leaves, lower surface: Close to 147B. Fully expanded leaves, upper surface: Close to N137A; venation, close to 138B. Fully expanded leaves, lower surface: Close to 147B; venation, close to 138C.

*Petioles.*—Length: About 1.3 cm. Diameter: About 3 mm. Texture, upper and lower surfaces: Fine pubescence; slightly rough. Color, upper surface: Close to 138B. Color, lower surface: Close to 138C.

Inflorescence description:

*Form and flowering habit.*—Decorative-type inflorescence form with ligulate-shaped ray florets; inflorescences borne on terminals above and beyond the foliar plane; disc and ray florets arranged acropetally on a capitulum; freely flowering habit with about 96 inflorescences developing per plant.

*Fragrance.*—Mildly fragrant; pungent, herbaceous.

*Flowering response.*—Early season flowering habit, plants exposed to natural season conditions begin flowering in mid to late August in the United Kingdom; plants flower uniformly and continuously.

*Inflorescence longevity.*—Inflorescences maintain good color and substance for about three to five weeks on the plant; inflorescences persistent.

*Inflorescence buds.*—Height: About 4 mm. Diameter: About 7 mm. Shape: Oblate. Color: Close to 143A.

*Inflorescence diameter.*—About 4.8 cm.

*Inflorescence height.*—About 2 cm.

*Disc diameter.*—About 6 mm.

*Receptacles.*—Height: About 3 mm. Diameter: About 4 mm. Shape: Conical. Color: Close to 145B.

*Ray florets.*—Number of ray florets per inflorescence: About 92 arranged in about six whorls. Orientation:

Initially upright, then about 75° from vertical. Length: About 2.2 cm. Width: About 7 mm. Shape: Ligulate. Apex: Emarginate. Base: Fused into a short tube. Margin: Entire. Texture, upper and lower surfaces: Smooth, glabrous; double-keeled. Color: When opening, upper surface: Close to 14A; towards the apex, close to 46A. When opening, lower surface: Close to N34A; towards the base, close to 9B. Fully opened, upper surface: Close to 9C; towards the apex, close to N34A; with development, color becoming closer to 6B and towards the apex, close to 34B. Fully opened, lower surface: Close to 9C; towards the apex, flushed with close to 34A; with development, color becoming closer to 6C and towards the apex, flushed with close to 34C.

*Disc florets*.—Number of disc florets per inflorescence: About 70 massed at the center of the receptacle. Length: About 4 mm. Diameter: About 1 mm. Shape: Tubular, elongated; apices, acute. Texture, inner and outer surfaces: Smooth, glabrous. Color, when opening: Apex: Close to 14A. Mid-section: Close to 1C. Base: Close to 155B. Color, fully opened: Apex: Close to 14B. Mid-section: Close to 1B. Base: Close to 155D.

*Phyllaries*.—Number of phyllaries per inflorescence: About 20 arranged in about three whorls. Length: About 6 mm. Width: About 2 mm. Shape: Ovate. Apex: Obtuse. Base: Obtuse. Margin: Entire. Texture, upper surface: Smooth, glabrous; waxy. Texture, lower surface: Fine pubescence; waxy. Color, upper surface: Close to 146A. Color, lower surface: Close to 146B.

*Peduncles*.—Length, terminal peduncle: About 2.2 cm. Diameter, terminal peduncle: About 2 mm. Angle: About 40° from vertical. Strength: Moderately strong; flexible. Texture: Densely pubescence. Color: Close to 138B.

*Reproductive organs*.—Androecium: None observed. Gynoecium: Present only on ray florets. Pistil length: About 4 mm. Stigma shape: Bi-parted. Stigma color: Close to 14B. Style length: About 3 mm. Style color: Close to 1B. Ovary color: Close to 155D.

*Seeds and fruits*.—Seed and fruit production has not been observed on plants of the new *Chrysanthemum*.

Disease & pest resistance: Resistance to pathogens and pests common to *Chrysanthemum* plants has not been observed on plants of the new *Chrysanthemum*.

Garden performance: Plants of the new *Chrysanthemum* have demonstrated good garden performance and to tolerate temperatures from about 0° C. to about 35° C.

It is claimed:

1. A new and distinct *Chrysanthemum* plant named 'Fidaysofla' as illustrated and described.

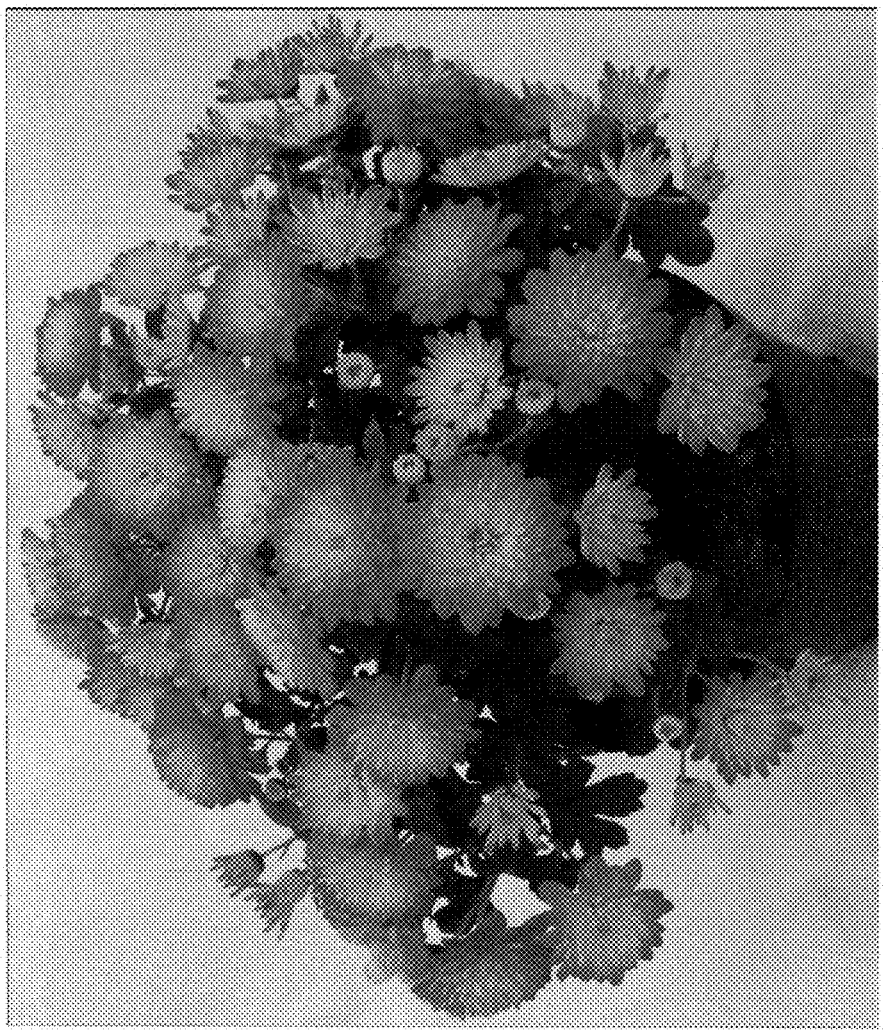

* * * * *